(12) United States Patent
Scirica et al.

(10) Patent No.: US 8,573,463 B2
(45) Date of Patent: Nov. 5, 2013

(54) LOCKING ARTICULATION MECHANISM

(75) Inventors: Paul Scirica, Huntington, CT (US); Kenneth M. Cappola, Monroe, CT (US)

(73) Assignee: Covidien LP, Mansfield, MA (US)

( * ) Notice: Subject to any disclaimer, the term of this patent is extended or adjusted under 35 U.S.C. 154(b) by 48 days.

(21) Appl. No.: 13/076,592

(22) Filed: Mar. 31, 2011

(65) Prior Publication Data
US 2012/0168484 A1 Jul. 5, 2012

(51) Int. Cl.
*A61B 17/04* (2006.01)
*A61B 17/10* (2006.01)

(52) U.S. Cl.
USPC ....................................................... 227/179.1

(58) Field of Classification Search
USPC .............. 227/175.1–182.1, 19; 606/219, 253, 606/256
See application file for complete search history.

(56) References Cited

U.S. PATENT DOCUMENTS

| | | | | |
|---|---|---|---|---|
| 3,820,645 | A * | 6/1974 | Davis | 400/134.4 |
| 4,491,132 | A * | 1/1985 | Aikins | 606/170 |
| 4,628,663 | A * | 12/1986 | Stanley et al. | 53/138.4 |
| 4,788,976 | A * | 12/1988 | Dee | 606/167 |
| 4,869,414 | A * | 9/1989 | Green et al. | 227/19 |
| 5,312,023 | A * | 5/1994 | Green et al. | 227/175.1 |
| 5,330,502 | A | 7/1994 | Hassler et al. | |
| 5,397,046 | A | 3/1995 | Savage et al. | |
| 5,482,197 | A | 1/1996 | Green et al. | |
| 5,485,952 | A * | 1/1996 | Fontayne | 227/178.1 |
| 5,575,799 | A | 11/1996 | Bolanos et al. | |
| 5,577,654 | A | 11/1996 | Bishop | |
| 5,584,425 | A | 12/1996 | Savage et al. | |
| 5,588,580 | A | 12/1996 | Paul et al. | |
| 5,588,581 | A | 12/1996 | Conlon et al. | |
| 5,626,587 | A | 5/1997 | Bishop et al. | |
| 5,673,840 | A | 10/1997 | Schulze et al. | |
| 5,673,841 | A | 10/1997 | Schulze et al. | |
| 5,702,408 | A | 12/1997 | Wales et al. | |
| 5,704,534 | A | 1/1998 | Huitema et al. | |
| 5,713,505 | A | 2/1998 | Huitema | |
| 5,762,255 | A * | 6/1998 | Chrisman et al. | 227/175.2 |
| 5,820,009 | A * | 10/1998 | Melling et al. | 227/176.1 |
| 5,823,066 | A | 10/1998 | Huitema et al. | |
| 5,855,311 | A | 1/1999 | Hamblin et al. | |

(Continued)

FOREIGN PATENT DOCUMENTS

| | | |
|---|---|---|
| EP | 2258281 | 12/2010 |
| WO | WO03/030743 | 4/2003 |
| WO | WO2005/037329 | 4/2005 |
| WO | WO2012/126783 | 9/2012 |

OTHER PUBLICATIONS

European Search Report EP12162578 dated Jan. 9, 2013.

*Primary Examiner* — Robert Long

(57) ABSTRACT

A surgical device including a handle assembly, an elongated body extending from the handle assembly, and an articulation mechanism connected to the handle assembly and configured to selectively articulate and lock an articulable tool assembly in one or more positions is provided. The articulation mechanism includes a main shaft member mounted for rotation and connected to an articulation linkage, a locking member configured to be received about the shaft portion of the main shaft member, the locking member defining a plurality of notches, an articulation handle fixedly secured to shaft portion of the main shaft member and configured for rotation relative to the locking member, and a lug member operatively mounted on the articulation handle and including a locking tab configured to be selectively received within a notch of the plurality of notches formed in the locking member.

20 Claims, 10 Drawing Sheets

(56) References Cited

U.S. PATENT DOCUMENTS

| | | |
|---|---|---|
| 5,862,715 A | 1/1999 | Lemire |
| 5,865,361 A | 2/1999 | Milliman |
| 5,901,895 A | 5/1999 | Heaton et al. |
| 6,540,737 B2 | 4/2003 | Bacher et al. |
| 6,716,232 B1 | 4/2004 | Vidal et al. |
| 6,786,382 B1 * | 9/2004 | Hoffman ................... 227/178.1 |
| 6,964,363 B2 | 11/2005 | Wales et al. |
| 6,981,628 B2 | 1/2006 | Wales |
| 6,993,808 B1 * | 2/2006 | Bennett et al. ................... 16/334 |
| 7,140,278 B2 * | 11/2006 | Neumann et al. ............ 81/427.5 |
| 7,143,924 B2 | 12/2006 | Scirica et al. |
| 7,191,751 B2 * | 3/2007 | Vick et al. .................. 123/185.2 |
| 7,303,107 B2 | 12/2007 | Milliman et al. |
| 7,328,828 B2 | 2/2008 | Ortiz et al. |
| 7,357,287 B2 * | 4/2008 | Shelton et al. ............. 227/178.1 |
| 7,419,080 B2 | 9/2008 | Smith et al. |
| 7,431,188 B1 | 10/2008 | Marczyk |
| 7,434,716 B2 | 10/2008 | Viola |
| 7,448,525 B2 * | 11/2008 | Shelton et al. ............. 227/176.1 |
| 7,455,208 B2 | 11/2008 | Wales et al. |
| 7,481,348 B2 | 1/2009 | Marczyk |
| 7,588,177 B2 | 9/2009 | Racenet et al. |
| 7,640,830 B2 | 1/2010 | Bonis |
| 7,654,431 B2 | 2/2010 | Hueil et al. |
| 7,670,334 B2 | 3/2010 | Hueil et al. |
| 7,690,547 B2 | 4/2010 | Racenet et al. |
| 7,694,865 B2 | 4/2010 | Scirica |
| 7,703,653 B2 | 4/2010 | Shah et al. |
| 7,753,904 B2 | 7/2010 | Shelton, IV et al. |
| 7,780,054 B2 | 8/2010 | Wales |
| 7,780,055 B2 | 8/2010 | Scirica et al. |
| 7,784,662 B2 | 8/2010 | Wales et al. |
| 7,793,814 B2 | 9/2010 | Racenet et al. |
| 7,815,091 B2 | 10/2010 | Marczyk |
| 7,819,896 B2 | 10/2010 | Racenet |
| 7,861,906 B2 | 1/2011 | Doll et al. |
| 7,870,810 B2 | 1/2011 | Da Dalt et al. |
| 7,909,220 B2 | 3/2011 | Viola |
| 7,918,230 B2 | 4/2011 | Whitman et al. |
| 7,981,011 B1 * | 7/2011 | Batca ............................ 482/100 |
| 8,057,508 B2 * | 11/2011 | Shelton, IV .................. 606/208 |
| 8,147,386 B2 * | 4/2012 | Farnsworth et al. ............ 482/54 |
| 8,336,754 B2 * | 12/2012 | Cappola et al. ............ 227/178.1 |
| 8,413,868 B2 * | 4/2013 | Cappola ..................... 227/176.1 |
| 2005/0006434 A1 | 1/2005 | Wales et al. |
| 2005/0184124 A1 * | 8/2005 | Scirica et al. .............. 227/176.1 |
| 2006/0094931 A1 | 5/2006 | Danitz et al. |
| 2008/0061108 A1 * | 3/2008 | Scirica ....................... 227/175.1 |
| 2008/0083807 A1 | 4/2008 | Beardsley et al. |
| 2008/0141744 A1 | 6/2008 | Desaphie et al. |
| 2008/0179375 A1 * | 7/2008 | Scirica ....................... 227/176.1 |
| 2009/0039137 A1 | 2/2009 | Viola |
| 2009/0088792 A1 | 4/2009 | Hoell, Jr. et al. |
| 2009/0114699 A1 | 5/2009 | Viola |
| 2009/0198272 A1 | 8/2009 | Kerver et al. |
| 2009/0206129 A1 * | 8/2009 | Doll et al. .................. 227/175.2 |
| 2009/0206130 A1 * | 8/2009 | Hall et al. .................. 227/175.2 |
| 2009/0206137 A1 * | 8/2009 | Hall et al. .................. 227/176.1 |
| 2010/0163596 A1 | 7/2010 | Marczyk |
| 2010/0163597 A1 | 7/2010 | Shah et al. |
| 2010/0237130 A1 | 9/2010 | Scirica |
| 2010/0320253 A1 * | 12/2010 | Marczyk .................... 227/176.1 |
| 2011/0062211 A1 | 3/2011 | Ross et al. |
| 2012/0138659 A1 * | 6/2012 | Marczyk et al. ........... 227/175.1 |

* cited by examiner

LOCKING ARTICULATION MECHANISM

BACKGROUND

1. Technical Field

The present disclosure relates to surgical instruments having one or more articulation portions. More particularly, the present disclosure relates to a mechanism for locking the articulating portion of the surgical instrument in a plurality of positions.

2. Background of Related Art

Various instruments have been modified for use in closed procedures, i.e., laparoscopic, arthroscopic, endoscopic. Such instruments typically include an elongated body portion configure to extend through an opening in a patient, i.e., through an access port, and/or thorough a natural orifice, e.g., anus, mouth.

Many of these instruments adapted for use in closed procedures include an articulable tool assembly mounted on a distal end of an elongated body portion. The tool assembly is controlled remotely from the handle assembly mounted on the proximal end of the elongated body portion. An articulation mechanism mounted on the handle assembly allows for the remote articulation of the tool assembly relative to the elongated body portion. Generally, the articulation mechanism includes a lever mounted on the handle assembly that, when turned, advances or retracts an articulation linkage. The articulation link extends through the elongated body portion and is operably connected to the tool assembly. Longitudinal advancement and retraction of the articulation linkage causes articulation of the tool assembly. The tool assembly is maintained in a desired position solely through the friction between the lever and the handle. In this manner, if a clinician were to accidentally contact the tool assembly with a structure within the body with sufficient force, the force could cause the tool assembly to be deflected from the desired position.

Therefore, it would be beneficial to have an articulation mechanism configured to selectively lock the tool assembly in one or more position.

SUMMARY

Accordingly, a surgical instrument including a locking articulation mechanism is provided.

DESCRIPTION OF THE DRAWINGS

Embodiments of a locking articulation mechanism are disclosed herein with reference to the drawings, wherein.

DETAILED DESCRIPTION

Embodiments of the presently disclosed locking articulation mechanism will now be described in detail with reference to the drawings wherein like numerals designate identical or corresponding elements in each of the several views. As is common in the art, the term "proximal" refers to that part or component closer to the user or operator, i.e. clinician, while the term "distal" refers to that part or component further away from the user. Although the articulation mechanism of the present disclosure will be described as it relates to a surgical device having a selectively attachable loading unit having a tool assembly, the presently disclosed articulation mechanism may be modified for use with other articulating surgical devices. For example, the tool assembly may have a removable and replaceable cartridge assembly.

Figure 1:
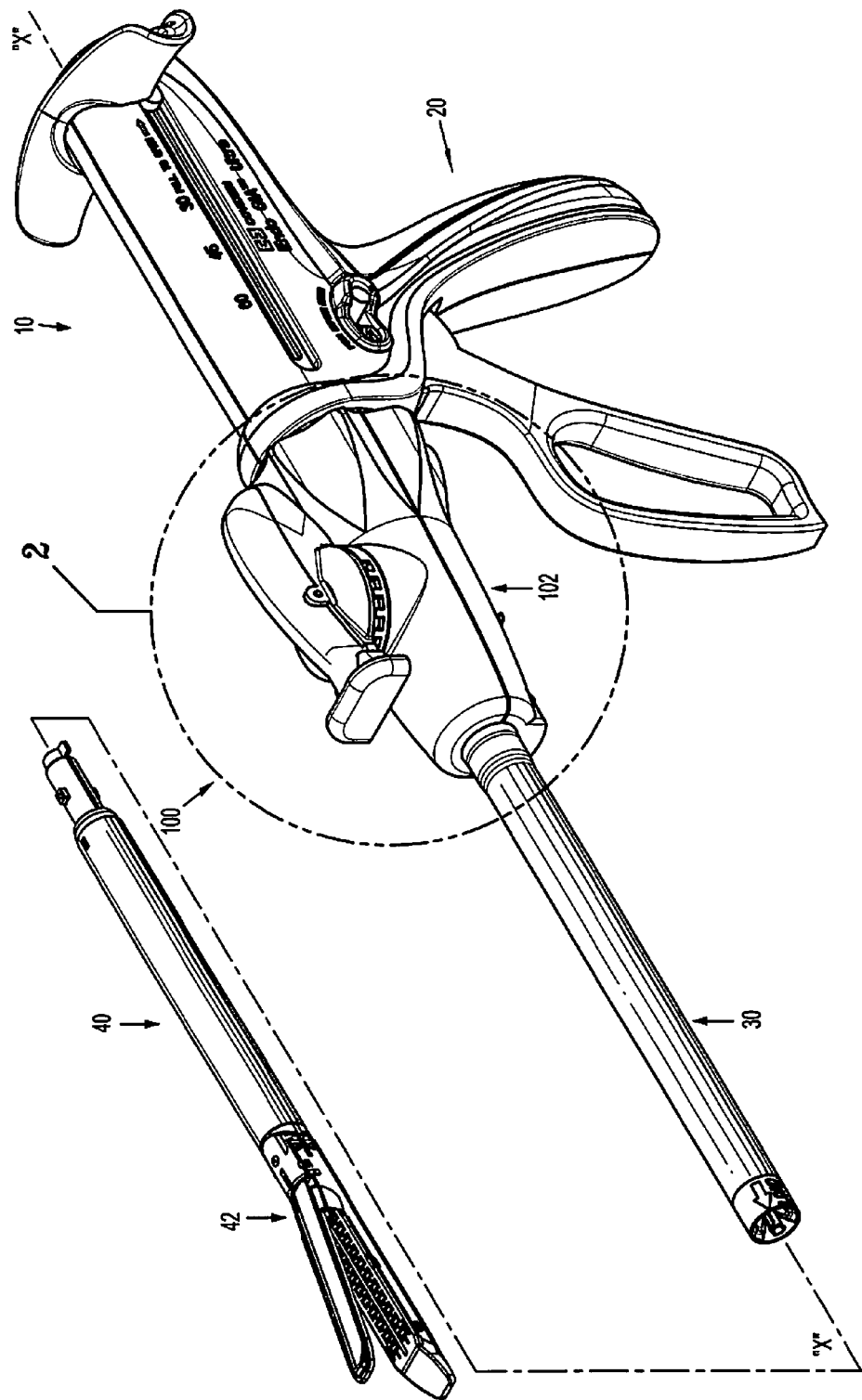
FIG. 1 is a perspective view of a surgical device including a locking articulation mechanism according to an embodiment of the present disclosure.

FIGS. 1-11 illustrate an embodiment of a locking articulation mechanism according to the present disclosure, shown generally as locking articulation mechanism 100. As shown in FIG. 1, and as will be discussed hereinbelow, locking articulation mechanism 100 is incorporated into a surgical device 10. Surgical device 10 includes a handle assembly 20 and an elongated body 30 extending from handle assembly 20. A distal end of elongated body 30 is configured to receive a loading unit 40 that includes an articulating tool assembly 42. Surgical device 10 may be configured for use in open or closed, i.e., laparoscopic, endoscopic, procedures. The structure and function of surgical device 10 will only be described herein to the extent necessary to fully disclose locking articulation mechanism 100. For a more detailed description of the structure and function of a surgical stapler, please refer to commonly owed U.S. Pat. No. 5,865,361 to Milliman et al., the content of which is hereby incorporated herein by reference, in its entirety.

Figure 2:
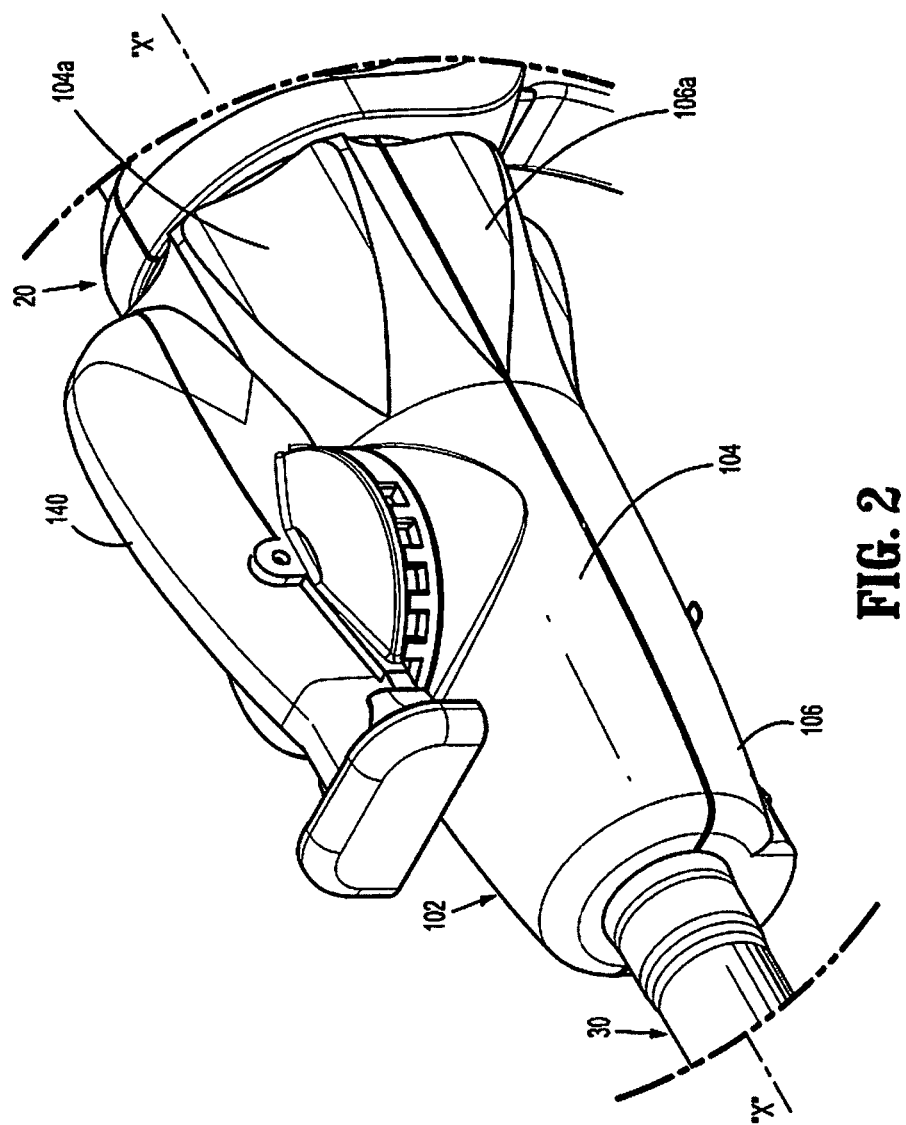
FIG. 2 is an enlarged perspective view of portion 2 of FIG. 1.
Figure 3:
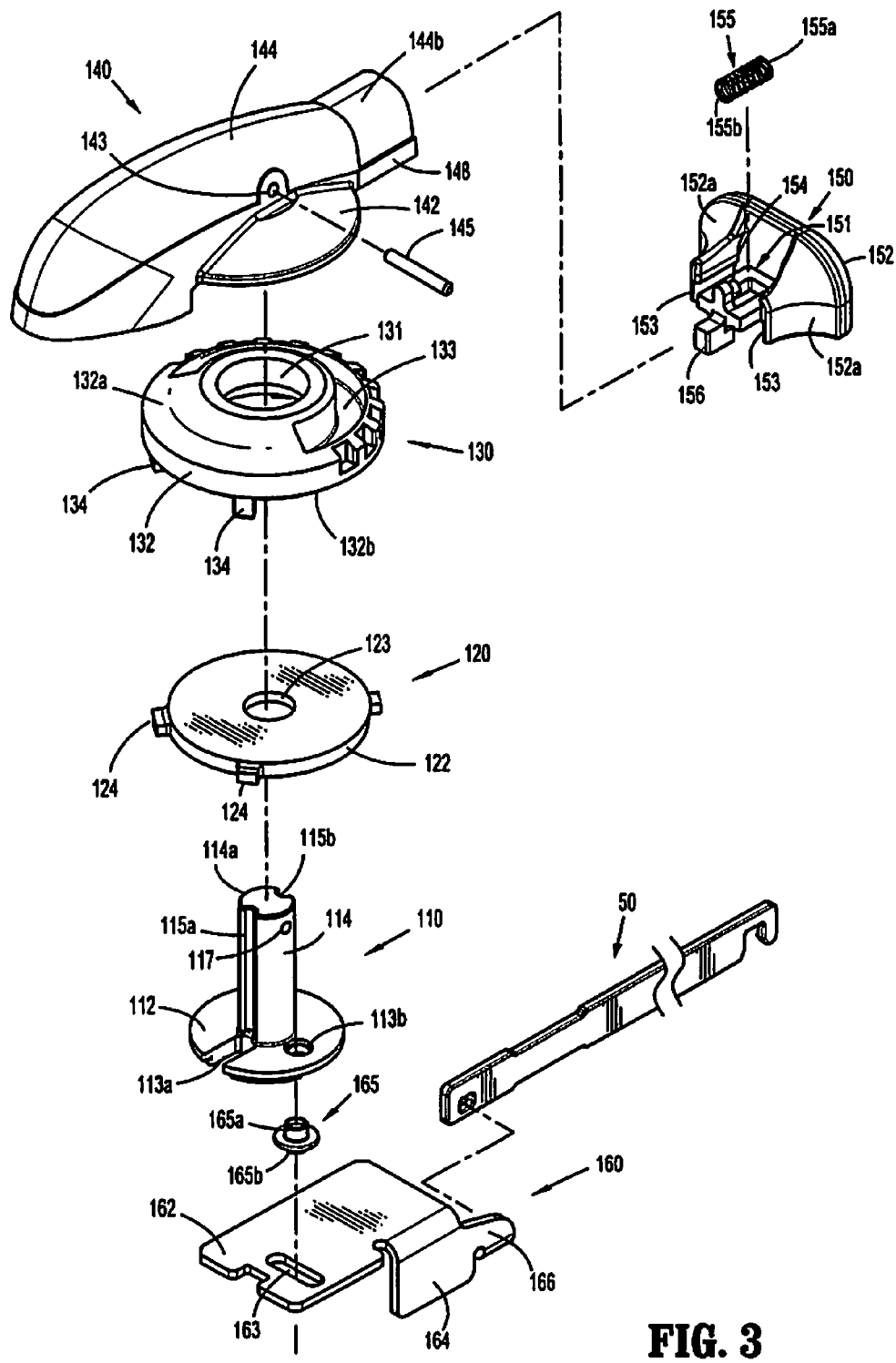
FIG. 3 is an exploded perspective view of the locking articulation mechanism of FIG. 1.

With reference now to FIGS. 1-3, articulation mechanism 100 includes an articulation housing 102 having upper and lower housing or knob halves 104, 106. Upper and lower housing halves 104, 106 are configured to be received about a distal end of handle assembly 20 and a proximal end of elongated body 30. Articulation housing 102 is configured to facilitate rotation of elongated body 30 about a longitudinal axis "x". Each of upper and lower housing halves 104, 106 include knurled proximal ends 104a, 106a configured for operable engagement by the user. Upper housing half 104 defines an opening 105 (FIG. 5) extending therethrough. Upper housing half 104 further defines a plurality of slots (not shown) extending radially outwardly of opening 105. As will be discussed in further detail below, the number of slots formed in upper housing half 104 corresponds in number and location with tabs 124 of retainer 120 and flanges 134 of locking member 130 (FIG. 4).

Figure 4:
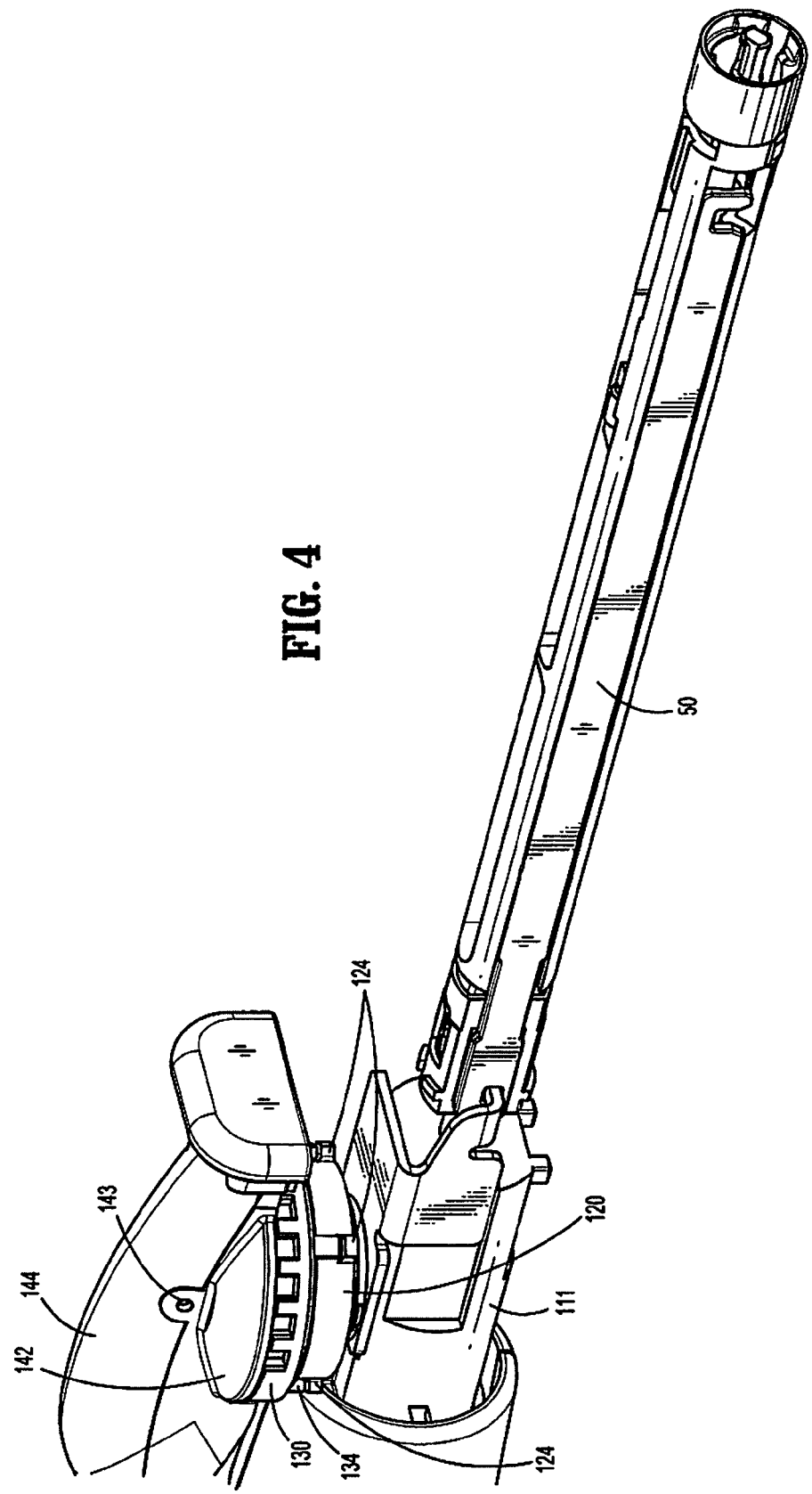
FIG. 4 is a cut-away side view of the locking articulation mechanism of FIG. 1.

With reference now to FIGS. 3 and 4, articulation mechanism 100 further includes a main shaft member 110, a retainer 120, a locking member or cover 130, an articulation lever 140, a lug member 150 and a channel yoke 160. As discussed above, the term "proximal" refers to that part or component closer to the user or operator. Since the user will engage lug member 150 and articulation handle 140 of articulation mechanism 100, reference will be made to articulation handle 140 being at a proximal end of locking articulation mechanism 100, while channel yoke 160 is located at a distal end thereof. The articulation handle 140 may be configured as a lever, knob, or the like.

Still referring to FIGS. 3 and 4, main shaft member 110 includes a base portion 112 and a shaft portion 114 extending from base portion 112. Base portion 112 is configured to be rotatably received within opening 105 (FIG. 5) of upper housing half 104. Base portion 112 includes a radially outward extending slot 113a. In one embodiment, slot 113a is configured to selectively receive a protrusion feature (not shown) of a sensor cap 111 shown in FIG. 5, extending, at least partially within articulation housing 102. Base portion 112 further includes an opening 113b formed therethrough. As will be discussed in further detail below, opening 113b is configured to engage a portion 165a of a cam pin 165 (FIG. 3). Shaft portion 114 of main shaft member 110 includes a pair of longitudinally extending notches 115a, 115b. Notches 115a, 115b form opposed substantially U-shaped recesses that extend substantially the length of shaft portion 114. Although shown having the same U-shape profile, recesses 115a, 115b may include alternatively shaped profiles and/or the profiles may differ in shape. Shaft portion 114 further includes an opening 117 extending radially through a proximal end 114a thereof. As will be discussed in further detail below, opening 117 is configured to receive a pin 145 (FIG. 3) to secure articulation lever 140 with main shaft 110.

With continued reference to FIGS. 3 and 4, retainer 120 forms a substantially planar member 122 including a plurality of radially outwardly extending tabs 124. As shown, planar member 122 includes four (4) tabs 124 corresponding in number and placement to slots (not shown) formed about opening 105 in upper housing half 104. The number and spacing of tabs 124 may vary to depending on the number and placement of the slots formed in upper housing half 104. It is contemplated that planar member 122 may include fewer tabs 124 than there are slots in upper housing half 102. Retainer 120 defines an opening 123 extending through the center of planar member 122. Opening 123 is sized to received about shaft portion 114 of main shaft member 110. With reference now to FIGS. 3-5, 7 and 8 locking member or cover 130 defines a substantially annular member 132 having a proximal surface 132a and a distal surface 132b. Proximal surface 132a is configured to engage and stabilize articulation lever 140. As shown, proximal surface 132a is inclined, however, other configurations, e.g., stepped, may be employed for stabilizing articulation lever 140. A plurality of feet 134 extend distally from annular member 132 for securing locking member 130 to upper housing half 104 of articulation housing 102. As shown, locking member 130 includes four (4) feet 134 evenly spaced about annular member 132. Locking member 130 may include more or less than four locking feet 134 that may or may not be evenly spaced about annular member 132.

With reference still to FIGS. 3-5, 7 and 8, annular member 132 of locking member 130 defines a longitudinal bore 131 extending therethrough and a semi-circular cut-out 133 radially spaced from longitudinal bore 131. As will be discussed in further detail below, cut-out 133 is configured to slidingly receive a flange 146 (FIG. 5) of articulation lever 140. Annular member 132 of locking member 130 further includes a plurality of notches 135 extending radially outward about semi-circular cut-out 133. Notches 135 are configured to receive a locking tab 156 of lug member 150. As will be discussed in further detail below, notches 135 are configured such that articulation mechanism 100 may selectively secure a tool assembly in predetermined articulated or non-articulated positions. Notches 135 may be evenly spaced, as shown, to permit incremental articulation of the tool assembly. Alternatively, notches 135 may include any other predetermined spacing, thereby resulting in predetermined incremental articulation of the tool assembly. As shown, a central notch 135a is formed in locking member 130 and is positioned such that when locking tab 156 of lug member 150 is received therein, articulation lever 140 is aligned with longitudinal axis "x", thereby securing the articulable tool assembly on surgical device 10 (FIG. 1) in a non-articulated position.

With reference now to FIGS. 3-6, articulation handle 140 includes a substantially circular base 142 and an elongated portion 144. Articulation handle 140 defines a recess 141 configured to receive an end 114a of shaft portion 114 of main shaft 110 and be received about annular body 132 of locking member 130. Articulation handle 140 further includes an opening 143 extending radially therethrough for receiving pin 145. Pin 145 is configured to fixedly secure articulation handle 140 to shaft portion 114 of main shaft member 110. The retainer holds the main shaft and the lever 140 down. For example, the locking member 130 flanges 134 can be used to hold down retainer flanges 124 which hold down main shaft and lever assembly.

Articulation handle 140 further includes a flange portion 146 (FIG. 5) extending distally therefrom. Flange portion 146 is configured to be slideably received within semi-circular cutout 133 of locking member 130. A first end 144a of elongated portion 144 is configured for engagement by a user. A second end 144b of elongated portion 144 is configured for operable engagement with lug member 150. Second end 144b of elongated portion 144 defines a recess 147 (FIG. 9) configured to receive a first end 155a of a biasing member 155. As shown, biasing member 155 includes a compression spring; however, any suitable biasing member may be employed. Second end 144b of elongated portion 144 further includes a pair of ridges 148 configured for operable engagement with lug member 150.

Figure 7:
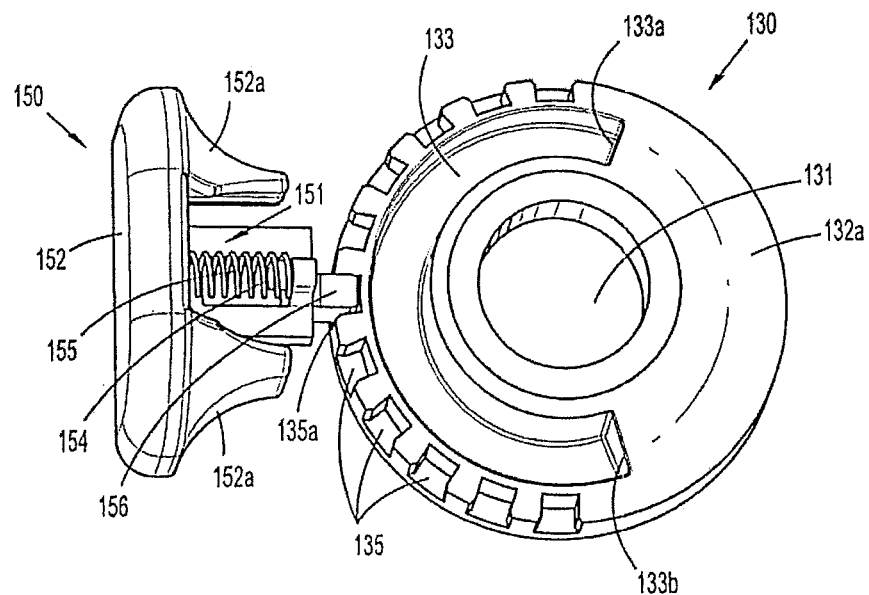
FIG. 7 is a top view of the locking cover and lug member of the locking articulation mechanism of FIG. 1, in an initial, locked position.
Figure 8:
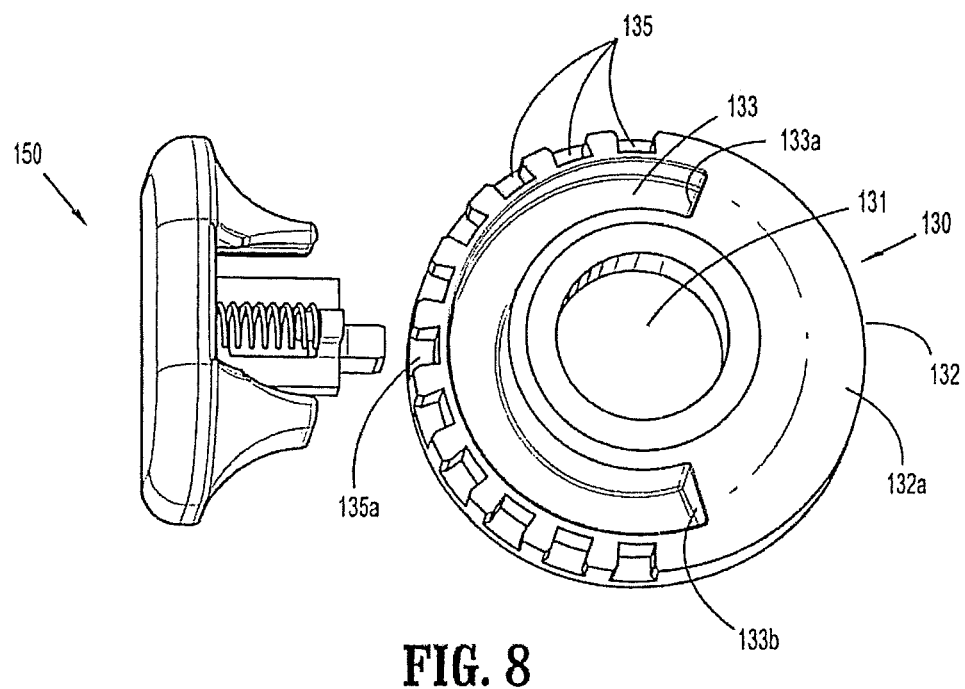
FIG. 8 is a top view of the locking cover and lug member of the locking articulation mechanism of FIG. 1, in a second, unlocked position.

With reference to FIGS. 3, 7 and 8, lug member 150 includes an engagement portion 152 configured for operable engagement by a user. As shown, engagement portion 152 includes a grip defining a pair of recesses 152a each configured to be engaged by one or more fingers and/or a thumb of a user. Although shown being configured for operable engagement by two or more fingers and/or a thumb of a user, it is envisioned that engagement portion 152 of lug member 150 may include any configuration suitable for selective engagement by a user.

Figure 5:
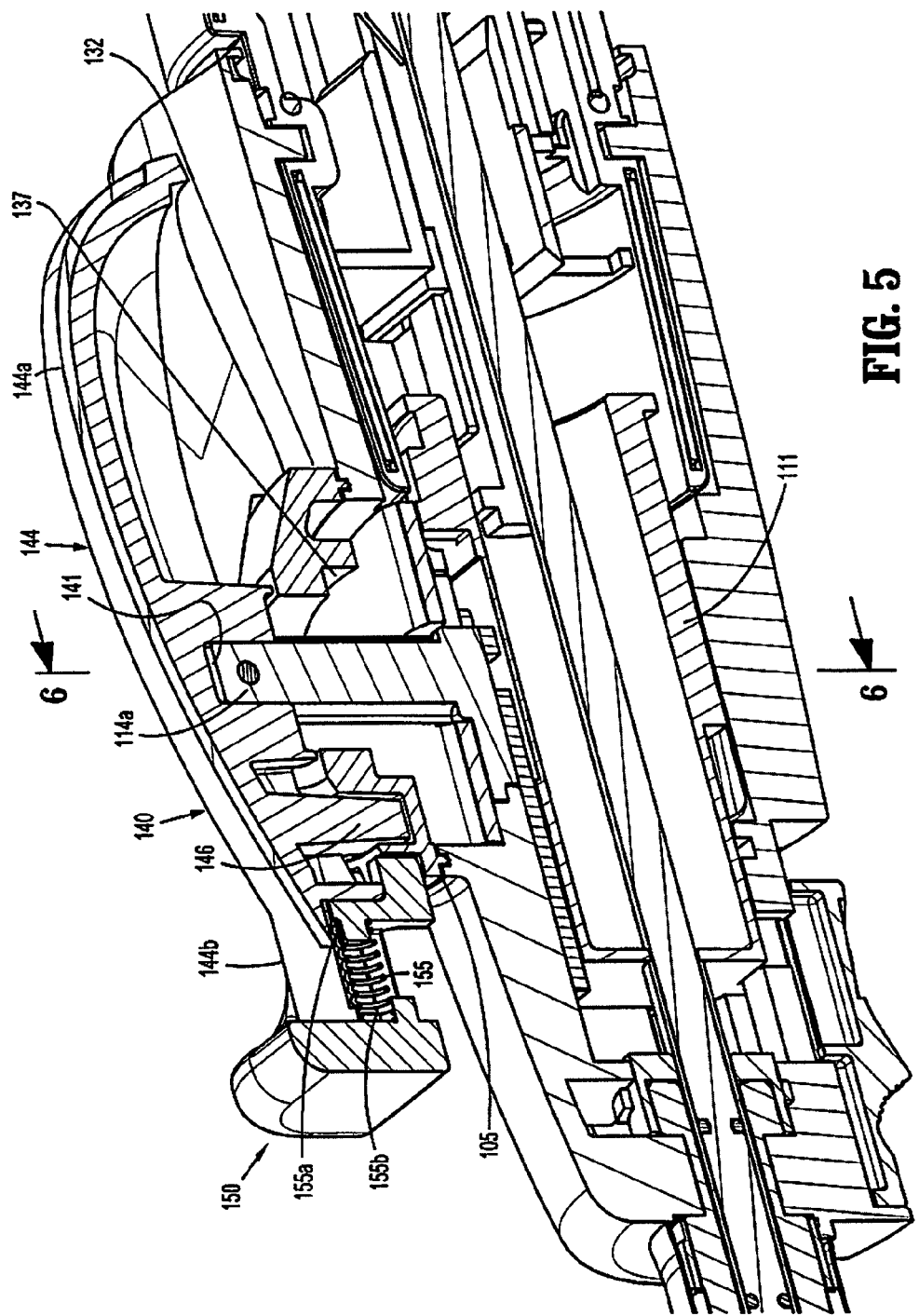
FIG. 5 is cross-sectional view of the locking articulation mechanism of FIG. 1.
Figure 6:
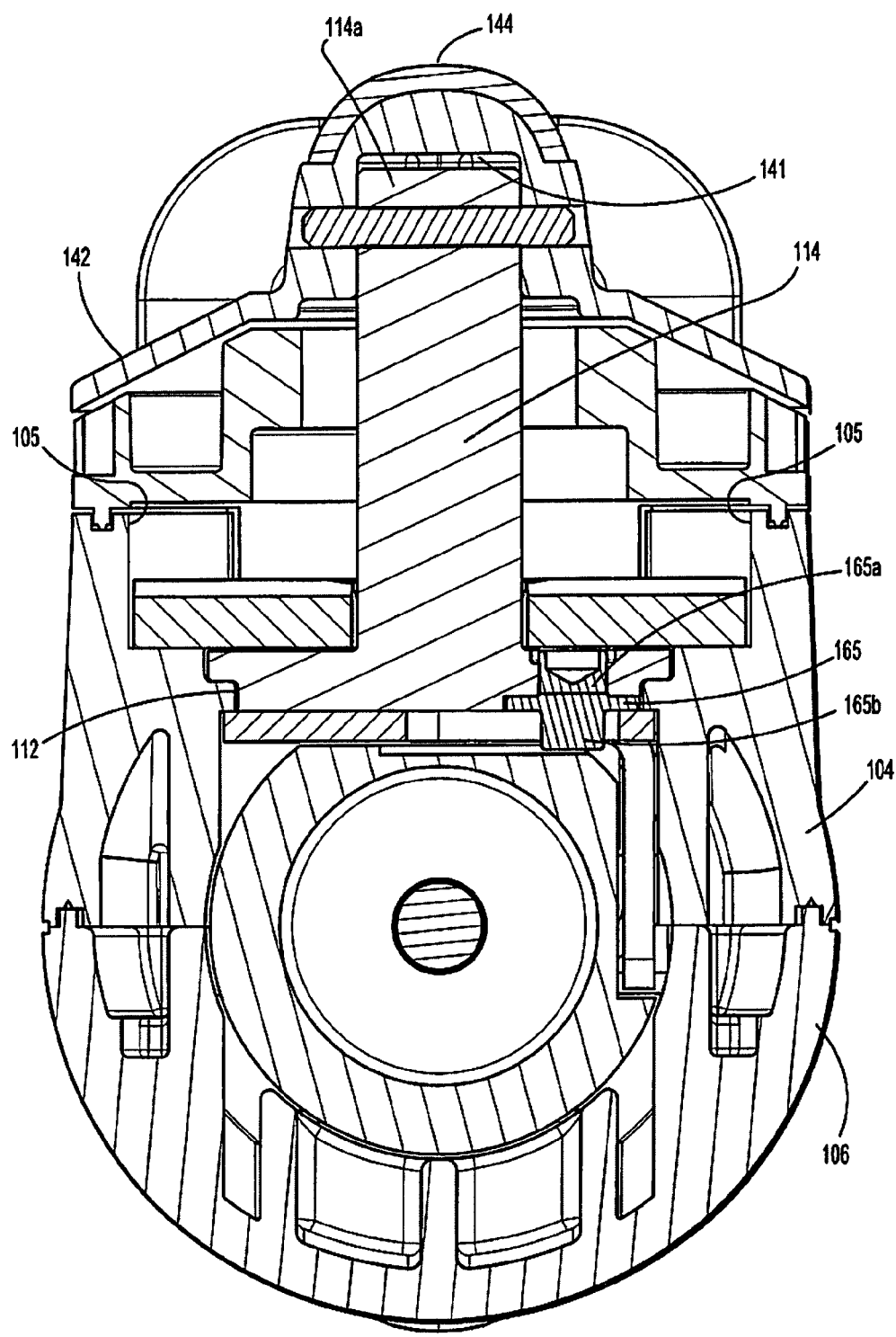
FIG. 6 is a cross-sectional view of the locking articulation mechanism of FIG. 1, taken along line 6-6 of FIG. 5.

With continued reference to FIGS. 3 and 5, lug member 150 defines a recess 151 configured to receive a portion of the articulation handle 140, such as second end 144b of the elongated portion 144 of the articulation handle 140. As shown, lug member 150 includes a pair of channels 153 configured to be slidingly received about ridges 148 on second end 144b of elongated portion 144. Lug member 150 includes a spring engagement tab 154 extending into recess 151 for engaging a second end 155b of biasing member 155. Lug member 150 further includes a locking tab 156 extending opposite from engagement portion 152. Locking tab 156 is configured for selective engagement within any of notches 135 formed in locking member 130.

With reference now to FIGS. 3 and 4, channel yoke 160 is a substantially L-shaped bracket having a horizontal portion 162 and a vertical portion 164. Extending from vertical member 164 is a flange 166. Flange 166 is configured to engage an articulation linkage 50, which, as discussed above, is operably connect to an articulable tool assembly (not shown). Horizontal member 162 defines a slot 163 configured to receive a distally extending portion 165b of cam pin 165.

The assembly of articulation mechanism 100 will now be described with reference to FIGS. 3-6. Prior to attaching upper and lower housing halves 104, 106 to elongated body 30 of surgical device 10, channel yoke 160 is positioned such that flange 166 formed on vertical member 164 of channel yoke 160 engages an articulation link 50 extending from within elongated body 30. As discussed above, longitudinal translation of articulation link 50 causes articulation of an articulable tool assembly. Upper and lower housing halves 104, 106 are then fit together about the proximal end of elongated body 30 and the distal end of handle assembly 20. Upper and lower housing halves 104, 106 may be joined with a snap fit connection, mechanical fasteners, bonding, adhesive or any other suitable method.

With reference still to FIGS. 3-6, cam pin 165 is next secured to base portion 112 of main shaft 110. Proximal portion 165a of cam pin 165 is received through opening 112b in base portion 112. In one embodiment, once portion 165a of cam pin 165 is received through opening 113b, proximal portion 165a is peened to secure cam pin 165 to main shaft 110. Alternatively, mechanical fasteners or other suitable methods may used to secure cam pin 165 to main shaft 110. In yet another embodiment, the positioning of articulation mechanism 100 165 relative to main shaft 110 maintains cam pin without any additional means. Once cam pin 165 is secured within opening 112b of in base portion 112, main shaft 110 is positioned within opening 105 of upper housing half 104 such that distal portion 165b of cam pin 165 is received within slot 163 formed in horizontal member 162 of channel yoke 160.

With continued reference to FIGS. 3-6, retainer 120 is next placed over and about shaft portion 114 of main shaft 110 and positioned such that tabs 124 extending radially outward therefrom are received within the slots formed about opening 105 of upper housing half 104. Locking member 130 is then received about shaft portion 114. Feet 134 of locking member 130 properly align locking member 130 with articulation housing 102. Alternatively, locking member 130 may be secured to upper housing half 104 with mechanical fasteners, adhesive, welding or other suitable methods.

Still referring to FIGS. 3-6, articulation handle 140 is next placed on end 114a of shaft 114 such that flange portion 146 of articulation handle 140 is received within semi-circular cut-out 133 of locking member 130. Locking pin 145 is then inserted through opening 117 formed in shaft portion 114 of main shaft 110 to secure articulation handle 140 to main shaft 110. Locking pin 155 may be secured within opening 117 by friction fit, adhesive or other suitable method.

With particular reference now to FIGS. 3 and 5, lug member 150 is next operably received on second end 144b of elongated portion 144 of articulation handle 140. Lug member 150 is positioned such that ridges 148 formed on second end 144b of elongated portion 144 are received within channels 153 formed in lug member 150. The lug member is biased in a direction toward the locking member. Biasing member 155, i.e., a compression spring, is received within recess 147 formed in second end 144b of elongated portion 144 with first end 155a of biasing member 155 engaging second end 144b of elongated portion 144 and second end 155b of biasing member 155 engaging spring engagement tab 154. In this manner, lug member 150 is biased inwardly within recess 147 of second end 144b and is configured to slide outward relative to second end 144b when a user engages engagement portion 152 thereof.

Figure 9:
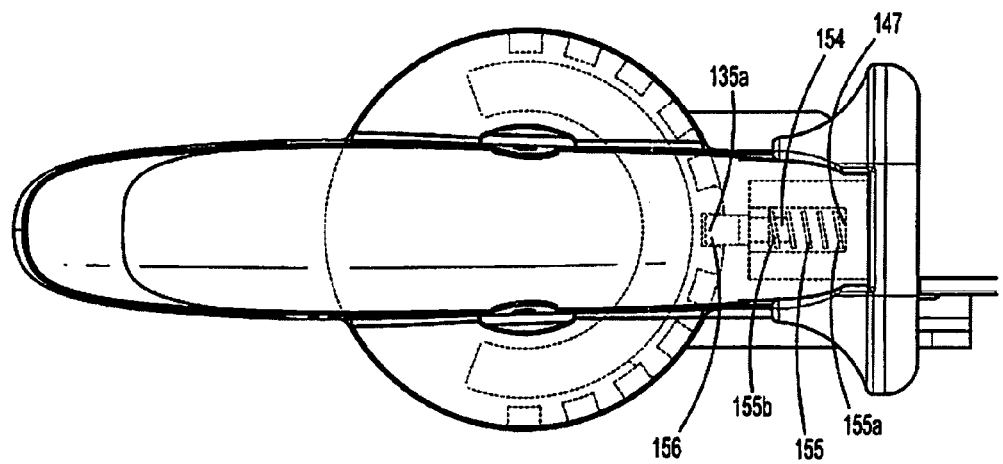
FIG. 9 is a top view of the locking articulation mechanism of FIG. 1 with the lug member in an initial or locked position and the articulation lever in a non-articulated position.

The use of articulation mechanism 100 will now be described with reference to FIGS. 1 and 9-11. Referring initially to FIGS. 1 and 9, articulation mechanism 100 is shown in an initial position. When articulation mechanism 100 is in the initial position, elongated body 30 and an articulable tool assembly (not shown) of surgical device 10 are in a non-articulated or straight configuration. In this configuration, locking tab 156 of lug member 150 is selectively received within central notch 135a of locking member 130.

Articulation mechanism 100 may be configured to interact with one or more computer and/or electronic components of an operating room system, or such components can be provided in the surgical device. This includes but is not limited to a sensor mechanism (not shown) of surgical device 10. In this manner, surgical device 10 includes a structure extending through elongated shaft 30 which includes a tubular or other shaped member (not shown) that is displaced upon the engagement with the distal end of the elongated body 30 by a replaceable loading unit that has an articulatable tool assembly (not shown). Loading units with tool assemblies that do not articulate do not displace the tubular member. A sensor cap (not shown) is arranged with the tubular member so as to be displaced. The sensor cap has a portion, such as a protrusion (not shown) that is received in slot 113a of main shaft 110 to prevent movement of main shaft 110 unless and until the sensor cap is displaced. In this way, articulation mechanism 100 may not be moved unless an articulable tool assembly is engaged with elongated body 30 of surgical device 10. Slot 113a is utilized to lock articulation mechanism 100 when a tool assembly is not loaded, to unlock articulation mechanism 100 when an articulatable tool assembly is loaded, and to lock articulation mechanism 100 when a non-articulable tool assembly is loaded. For a more detailed discussion of the structure and function of the sensor mechanism, please refer to previously noted U.S. Pat. No. 5,865,361 to Milliman et al.

Figure 10:
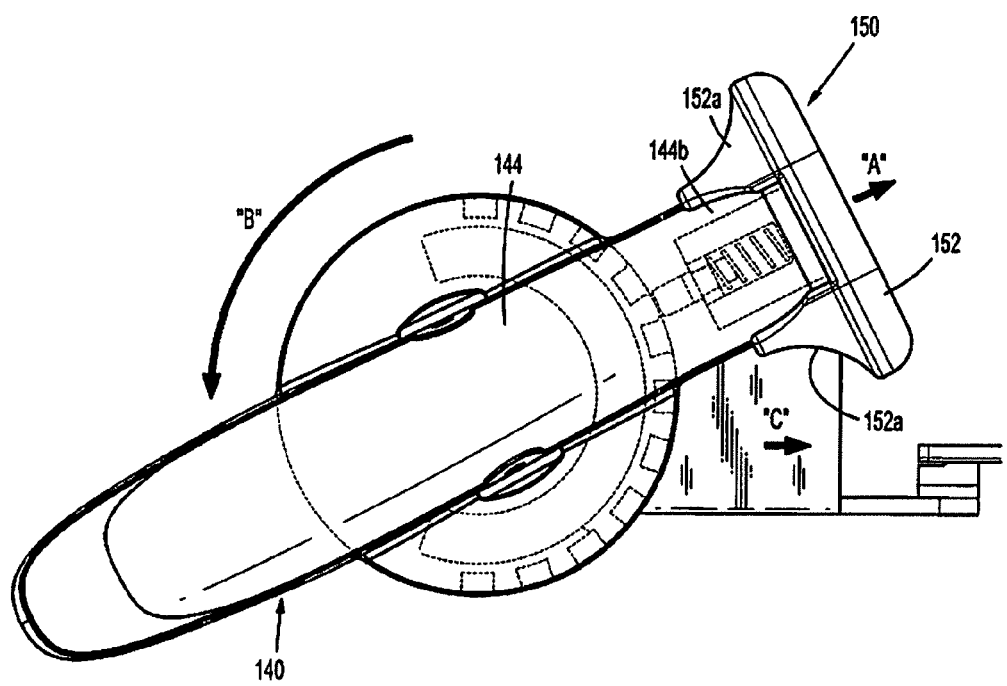
FIG. 10 is a top view of the locking articulation mechanism of FIG. 1 with the lug member in a second or unlocked position and the articulation lever in an articulated position.

Turning now to FIG. 10, engagement of recesses 152a of engagement portion 152 of lug member 150 by a user and subsequent retraction of lug member 150 relative to second end 144b of elongate portion 144, in the direction of arrow "A", causes retraction of locking tab 156 of lug member 150 from within central notch 135a of locking member 130. In this second or unlocked position, articulation handle 140 is free to rotate relative to locking member 130. As shown in FIG. 10, counter-clockwise rotation of articulation handle 140 relative to locking member 130, in the direction of arrow "B", results in advancement of yoke 160, and attached articulation linkage 50, in the direction of arrow "C". As discussed above, articulation handle 140 is securely attached to shaft portion 114 of main shaft 110 such that rotation of articulation handle 140 turns main shaft 110. Base portion 112 of main shaft 110 is connected to yoke 160 by cam member 165 such that the rotation of main shaft 110 in a first direction causes advancement of articulation linkage 50 while rotation of main shaft 110 in a second direction causes retraction of articulation linkage 50. Advancement and retraction of articulation linkage 50 results in articulation of a tool assembly in respective first and second directions. The amount of rotation of articulation handle 140 is limited by the engagement of flange portion 146 of articulation handle 140 with first and second end walls 133a, 133b (FIGS. 7 and 8) of semi-circular cut-out 133 of locking member 130.

Figure 11:
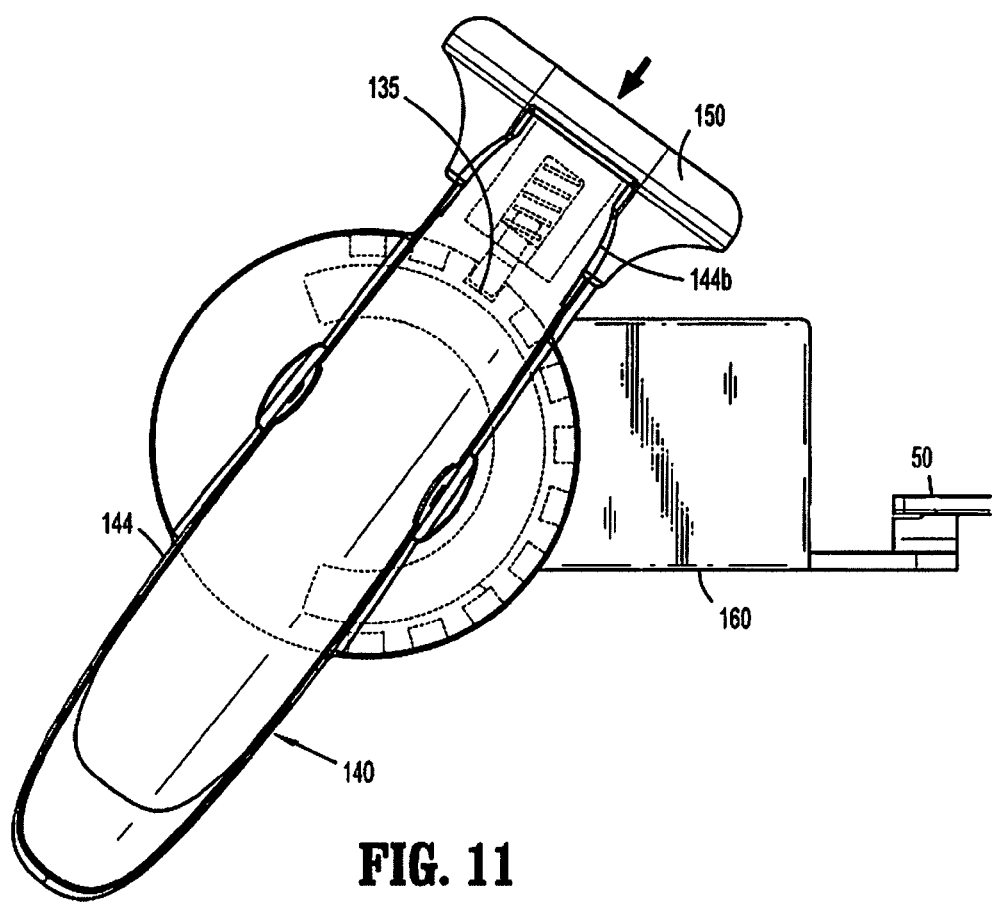
FIG. 11 is a top view of the locking articulation mechanism of FIG. 1 with the lug member in the initial or locked position and the articulation lever in a further articulated position.

With reference to FIG. 11, release of lug member 150 by the clinician permits the return of lug member 150 to an initial, non-retracted position. Lug member 150 is biased to the initial position by compression spring 155. The return of lug member 150 to the initial position results in locking tab 156 being received within notch 135, thereby locking articulation handle 140 relative to locking member 130. In this manner, an articulable tool assembly (not shown) mounted on the distal end of elongate body 30 (FIG. 1) is locked in an articulated position. The tool assembly may be further articulated or returned to the initial, non-articulated position by retracting lug member 150 relative to second end 144b of elongated portion 144 and rotating articulation handle 140 relative to locking member 130.

Figure 12:
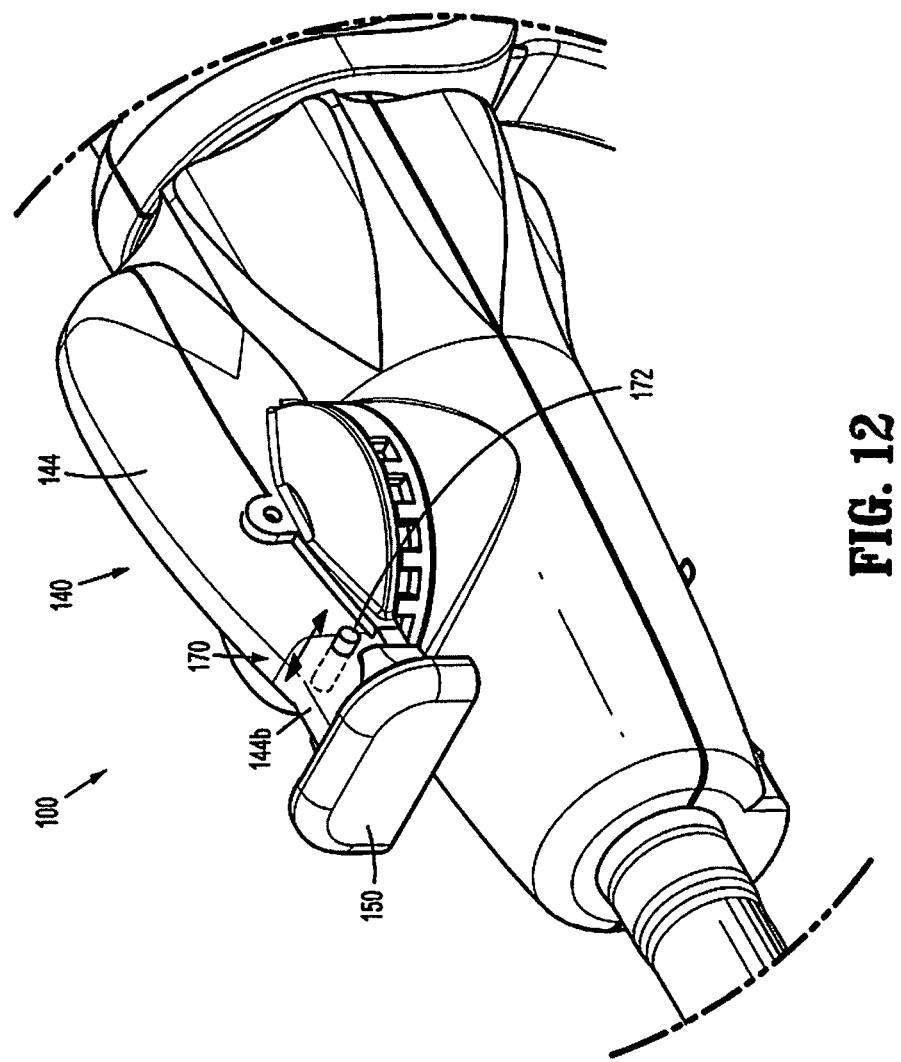
FIG. 12 is an enlarged perspective view of an articulation lever according to another embodiment of the present disclosure.

It will be understood that various modifications may be made to the embodiment disclosed herein. For example, with reference to FIG. 12, articulation mechanism 100 may further include a locking mechanism 170 for selectively locking lug member 150 relative to elongated portion 144 of articulation handle 140. As shown, locking mechanism 170 includes a side mounted button 172 extending through second end 144b of elongated portion 144. Button 172 is configured to selectively engage lug member 150 to prevent unlocking of articulation handle 140 relative to locking member 130. Alternatively, articulation mechanism 100 may include a locking mechanism (not shown) that requires advancing lug member 150 relative to elongated portion 144 of articulation handle 140 prior to being able to retract lug member 150 relative thereto. Therefore, the above description should not be construed as limiting, but merely as exemplifications of particular embodiments. Those skilled in the art will envision other modifications within the scope and spirit of the claims appended hereto.

The invention claimed is:

1. A surgical device comprising:
   a handle assembly;
   an elongated body extending from the handle assembly; and
   an articulation mechanism operably connected to the handle assembly and configured to selectively articulate and lock an articulatable tool assembly in one or more positions, the articulation mechanism including:
   a main shaft member mounted for rotation and connected to an articulation linkage;
   a locking member configured to be received about the main shaft member and rotationally fixed relative to the elongated body, the locking member defining a plurality of notches;
   an articulation handle fixedly secured to the main shaft member and configured for rotation relative to the locking member; and
   a lug member mounted on the articulation handle being configured to rotate with the articulation handle, at least a portion of the lug member being mounted for being selectively received within a notch of the plurality of notches when in a first position, and for being disposed radially outward of the plurality of notches when in a second position, the lug being inwardly biased toward the first position.

2. The surgical device of claim 1, further including an articulatable tool assembly mounted on a distal end of the elongated body.

3. The surgical device of claim 1, wherein the plurality of notches are evenly spaced.

4. The surgical device of claim 1, where the plurality of notches includes a central notch for reception of the lug member when the surgical device is in a non-articulated position.

5. The surgical device of claim 1, wherein the articulation handle includes a flange configured to be received within a cutout in the locking member to limit rotation of the articulation handle.

6. The surgical device of claim 1, further including a yoke attached to the main shaft member and the articulation linkage.

7. The surgical device of claim 1, further including a locking mechanism for selectively locking the lug member relative to the articulation handle.

8. The surgical device of claim 2, wherein the tool assembly includes an anvil and a staple cartridge assembly.

9. The surgical device of claim 1, further comprising a retainer rotationally fixed with respect to the handle assembly.

10. The surgical device of claim 9, wherein the retainer has an opening for receiving the main shaft member.

11. The surgical device of claim 1, wherein the lug member defines a recess configured to receive a portion of the articulation handle.

12. The surgical device of claim 11, wherein the lug member is biased in a direction toward the locking member.

13. The surgical device of claim 1, further comprising a sensor cap having a portion thereof receivable in a slot of the main shaft.

14. The surgical device of claim 13, further comprising a loading unit having the articulatable tool assembly, the loading unit being configured to displace the sensor cap so that the portion of the sensor cap moves away from the main shaft.

15. The surgical device of claim 1, wherein the lug member includes an engagement portion configured for operable engagement by a user.

16. The surgical device of claim 1, wherein the articulation mechanism further includes a spring for biasing the lug member radially inward towards the locking member.

17. The surgical device of claim 1, wherein the lug member extends distally from the handle assembly.

18. A surgical device comprising:
   a handle assembly;
   an elongated body extending from the handle assembly; and
   an articulation mechanism operably connected to the handle assembly and configured to selectively articulate and lock an articulatable tool assembly in one or more positions, the articulation mechanism including:
   a main shaft member mounted for rotation and connected to an articulation linkage;
   a locking member configured to be received about the main shaft member and rotationally fixed relative to the elongated body, the locking member defining a plurality of notches;
   an articulation handle fixedly secured to the main shaft member and configured for rotation relative to the locking member; and
   a lug member mounted on the articulation handle being configured to rotate with the articulation handle including an engagement portion for operable engagement by a user, at least a portion of the lug member being mounted for being selectively received within a notch of the plurality of notches formed in the locking member.

19. The surgical device of claim 1, wherein the lug member being finger-operable by a user.

20. The surgical device of claim 18, wherein the lug member being finger-operable by a user.

* * * * *